United States Patent
Yanagita et al.

(10) Patent No.: US 7,446,319 B2
(45) Date of Patent: Nov. 4, 2008

(54) SEMICONDUCTOR RADIATION DETECTOR AND RADIOLOGICAL IMAGING APPARATUS

(75) Inventors: Norihito Yanagita, Hitachi (JP); Hiroshi Kitaguchi, Naka (JP); Takafumi Ishitsu, Hitachi (JP); Kensuke Amemiya, Hitachinaka (JP); Yuuichirou Ueno, Hitachi (JP); Katsutoshi Tsuchiya, Hitachi (JP); Shinichi Kojima, Hitachi (JP); Kazuma Yokoi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/874,225

(22) Filed: Jun. 24, 2004

(65) Prior Publication Data

US 2005/0067577 A1 Mar. 31, 2005

(30) Foreign Application Priority Data

Sep. 30, 2003 (JP) ............................. 2003-341937

(51) Int. Cl.
*G01T 1/164* (2006.01)
(52) U.S. Cl. ............................. 250/370.09; 250/370.01
(58) Field of Classification Search ............ 250/370.09, 250/370.01
See application file for complete search history.

(56) References Cited

U.S. PATENT DOCUMENTS

| | | | | |
|---|---|---|---|---|
| 4,926,052 A | * | 5/1990 | Hatayama et al. | ...... 250/370.14 |
| 5,907,156 A | | 5/1999 | Nishizawa et al. | |
| 6,621,084 B1 | | 9/2003 | Wainer et al. | |
| 6,657,180 B1 | * | 12/2003 | Monnet et al. | ............ 250/214.1 |
| 7,026,622 B2 | | 4/2006 | Kojima et al. | |
| 2001/0023980 A1 | | 9/2001 | Ohmori | |
| 2002/0153492 A1 | * | 10/2002 | Sekine et al. | ........... 250/370.11 |
| 2003/0034456 A1 | | 2/2003 | McGregor | |
| 2003/0047679 A1 | * | 3/2003 | Cornish et al. | ............... 250/287 |
| 2005/0258369 A1 | * | 11/2005 | Wieczorek | ................... 250/366 |

FOREIGN PATENT DOCUMENTS

| | | |
|---|---|---|
| EP | 1 336 377 A2 | 8/2003 |
| JP | 60073484 | 4/1985 |
| JP | 60-209195 | 10/1985 |
| JP | 62-251688 | 11/1987 |
| JP | 11-304930 | 11/1999 |
| JP | 2000-307145 | 11/2000 |
| JP | 2003-84068 | 3/2003 |
| JP | 2003084068 | * 3/2003 |
| JP | 2003-167058 | 6/2003 |
| JP | 3427584 | 7/2003 |

* cited by examiner

*Primary Examiner*—Sharon E. Payne
*Assistant Examiner*—Mary Zettl
(74) *Attorney, Agent, or Firm*—Dickstein Shapiro LLP

(57) ABSTRACT

A radiation imaging apparatus with high spatial resolution including semiconductor radiation detectors arranged on a wiring board capable of detecting γ-rays by separating their positions in the direction of incidence of γ-rays is provided. A semiconductor radiation detector is constructed by including five semiconductor devices made up of, for example, CdTe rectangular parallelepiped plates, a cathode electrode on one side of the semiconductor device, an anode electrode on the other side of the semiconductor device and an insulator for coating five semiconductor detection devices from the outside. The semiconductor radiation detector is mounted on a wiring board using an anode pin and a cathode pin.

6 Claims, 14 Drawing Sheets

SEMICONDUCTOR RADIATION DETECTOR AND RADIOLOGICAL IMAGING APPARATUS

BACKGROUND OF THE INVENTION

The present invention relates to a semiconductor radiation detector, which allows semiconductor radiation detectors to be arranged in a three-dimensional direction and a radiation imaging apparatus using the same.

A semiconductor radiation detector is provided with a semiconductor device made of CdTe, CdZnTe, etc., and electrodes formed on both sides of this semiconductor device designed to pick up electric charge generated when radiation such as X-rays or γ-rays enter the semiconductor device by applying a bias voltage between these electrodes from the electrodes as a signal.

When a semiconductor radiation detector is used for a medical radiation imaging apparatus, etc., the semiconductor radiation detector is connected on a wiring board to form a radiation detection section (see JP-A-2003-84068 (paragraph 00024, FIG. 3), for example).

A PET (Positron Emission Tomography), which is a kind of a medical radiation imaging apparatus, is intended to improve spatial resolution. However, the device described in JP-A-2003-84068 can detect γ-rays mainly on a plane of incidence of γ-rays (e.g., X-Y plane) by separating their positions but cannot detect γ-rays in the direction of incidence of γ-rays (e.g., Z-direction) by separating the positions. That is, the device cannot detect γ-rays by separating the positions in the three-dimensional direction. Thus, it cannot improve spatial resolution sufficiently.

It is an object of the present invention to provide a semiconductor radiation detector and radiation imaging apparatus capable of improving spatial resolution.

SUMMARY OF THE INVENTION

A feature of a first embodiment of the invention for solving the above described problem is a semiconductor radiation detector comprising a plurality of semiconductor detection devices, each having an anode electrode on one side of a semiconductor device and a cathode electrode on the other side, arranged in parallel and an insulator which coats at least a portion of the semiconductor detection devices from the outside. This enables the semiconductor radiation detector to be arranged in an arbitrary position and its spatial resolution to be improved.

The semiconductor radiation detector preferably has a structure in which internal wiring is provided in the interior or on the surface of the insulator for transmitting electrical signals from cathode and anode signals.

A feature of a second embodiment of the invention for solving the above described problem is a detector module comprising a semiconductor radiation detector and a wiring board, wherein the semiconductor radiation detector comprises a plurality of semiconductor detection devices, each having a cathode electrode on one side of a semiconductor device and an anode electrode on the other side arranged in parallel in such a way that the cathode electrodes of the neighboring semiconductor detection devices are opposed to each other and an insulator which coats at least a portion of the semiconductor detection devices from the outside, wherein the cathode electrode is connected to a first wiring provided on the wiring board through a pin and the anode electrode is connected to a second wiring provided on the wiring board through another pin.

Furthermore, a feature of a third embodiment of the invention for solving the above described problem is a detector module comprising a semiconductor radiation detector and a first wiring board, wherein the semiconductor radiation detector comprises a plurality of semiconductor detection devices, each having a cathode electrode on one side of a semiconductor device and an anode electrode on the other side, arranged in parallel in such a way that the cathode electrodes are opposed to each other and the anode electrodes are opposed to each other, a second wiring board is disposed between the neighboring cathode electrodes, the respective cathode electrodes are connected to a plurality of second wirings provided on the second wiring board, a third wiring board is disposed between the neighboring anode electrodes and the respective anode electrodes are connected to a plurality of third wirings provided on the third wiring board, wherein the semiconductor radiation detector is disposed on the first wiring board, and the second wiring of the second wiring board is connected to the first wiring provided on the first wiring board and the third wiring of the third wiring board is connected to a fourth wiring provided on the first wiring board.

The second and third wiring boards preferably comprise a wiring board having flexibility, for example, an FPC (Flexible Printed Circuit).

The present invention makes it possible to detect γ-rays by separating their positions in the direction of incidence of γ-rays, too, and further detect positions separately in the three-dimensional direction. As a result, spatial resolution can be improved. Furthermore, the first and second embodiments have another effect of allowing the semiconductor radiation detector to be replaced, for example, enabling a semiconductor radiation detector to be detached or attached individually. Furthermore, the third embodiment can arrange the semiconductor detection devices extremely densely and consequently has the effect of improving sensitivity, too.

Other objects, features and advantages of the invention will become apparent from the following description of the embodiments of the invention taken in conjunction with the accompanying drawings.

DESCRIPTION OF THE EMBODIMENTS

With reference now to the attached drawings of FIGS. 1 to 5, a first embodiment of the present invention will be explained below.

First Embodiment

Figure 1:
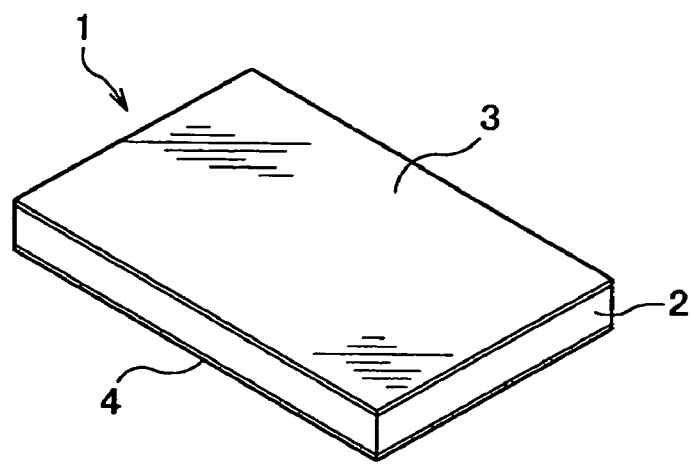
FIG. 1 is a perspective view of a semiconductor radiation detection device used for a semiconductor radiation detector according to a first embodiment of the present invention.

Reference numeral 1 in FIG. 1 denotes a radiation detection device and this radiation detection device 1 is constructed by including five semiconductor devices 2 (see FIG. 2) made up of a rectangular flat plate made of, for example, CdTe, cathode electrodes 3 (Pt, etc.) formed into a thin-film shape on one side of each semiconductor device 2 by means of, for example, vapor deposition, anode electrodes 4 (In, etc.) formed into a thin-film shape on the other side of the semiconductor device 2 and a rectangular parallelepiped elastic insulator 5 (see FIG. 2) which covers the five semiconductor devices 2 from the outside.

Figure 2:
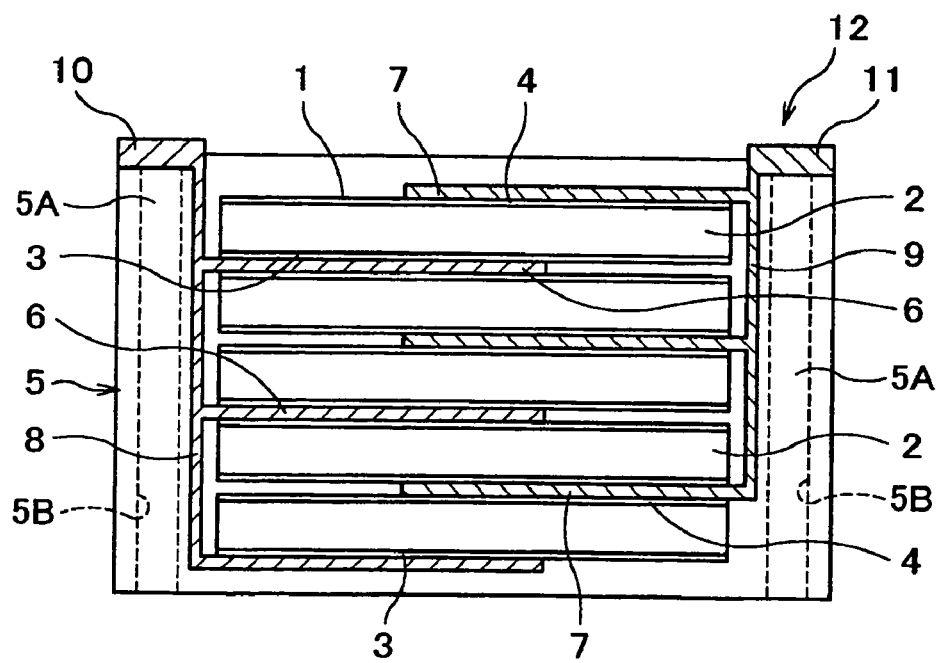
FIG. 2 is a cross-sectional view showing the semiconductor radiation detector according to the first embodiment of the present invention.
Figure 3:
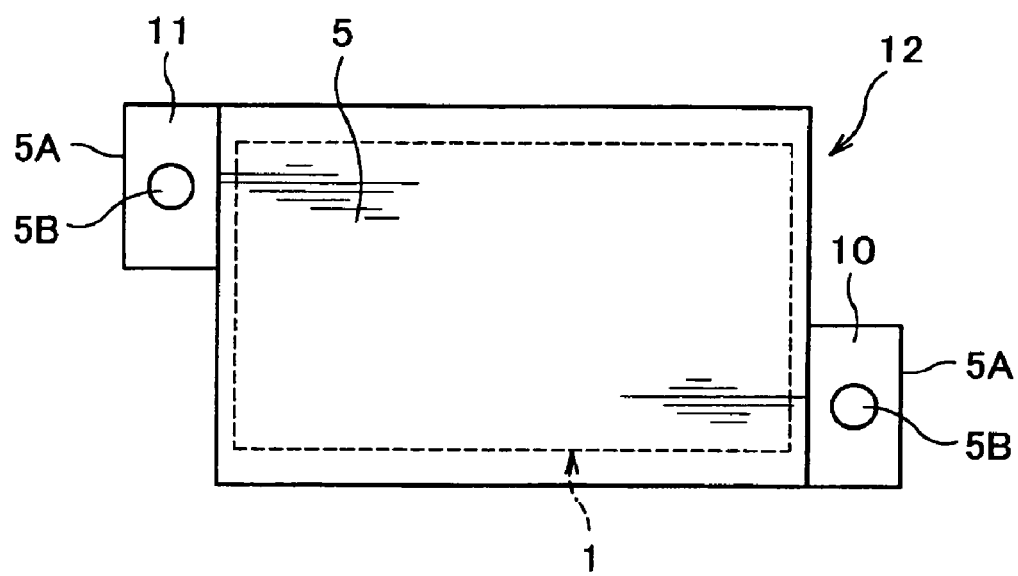
FIG. 3 is a plan view of the semiconductor radiation detector according to the first embodiment of the present invention.

As shown in FIG. 2, this semiconductor radiation device 1 consists of five semiconductor devices 2 stacked together. Furthermore, conductive cathode-side thin plates 6 are pasted to the respective cathode electrodes 3 and conductive anode-side thin plates 7 are pasted to the respective anode electrodes 4. First and second internal wirings 8, 9 provide connections among the thin plates 6 and the thin plates 7, respectively. Furthermore, rectangular parallelepiped brackets 5A, 5A are formed integral with the insulator 5 on both sides in its width direction and pin insertion holes 5B are formed in these brackets 5A in the longitudinal direction thereof so that a cathode pin 29 and an anode pin 30 which will be described later are inserted therein. Furthermore, a cathode terminal 10 to be connected to the first internal wiring 8 is exposed from an end face of the one bracket 5A to the outside and an anode terminal 11 to be connected to the second internal wiring 9 is exposed from an end face of the other bracket 5A to the outside. The semiconductor devices 2, cathode electrodes 3, anode electrodes 4, insulator 5, thin plates 6, 7, internal wirings 8, 9, cathode terminal 10 and anode terminal 11 constitute a semiconductor radiation detector 12. Note that the structures of the first internal wiring 8 and cathode terminal 10, and the second internal wiring 9 and anode terminal 11 can be simplified by forming inner walls of the respective pin insertion holes 5B using a conductive material and connecting the thin plates 6 and 7 with the conductive inner walls.

Figure 4:
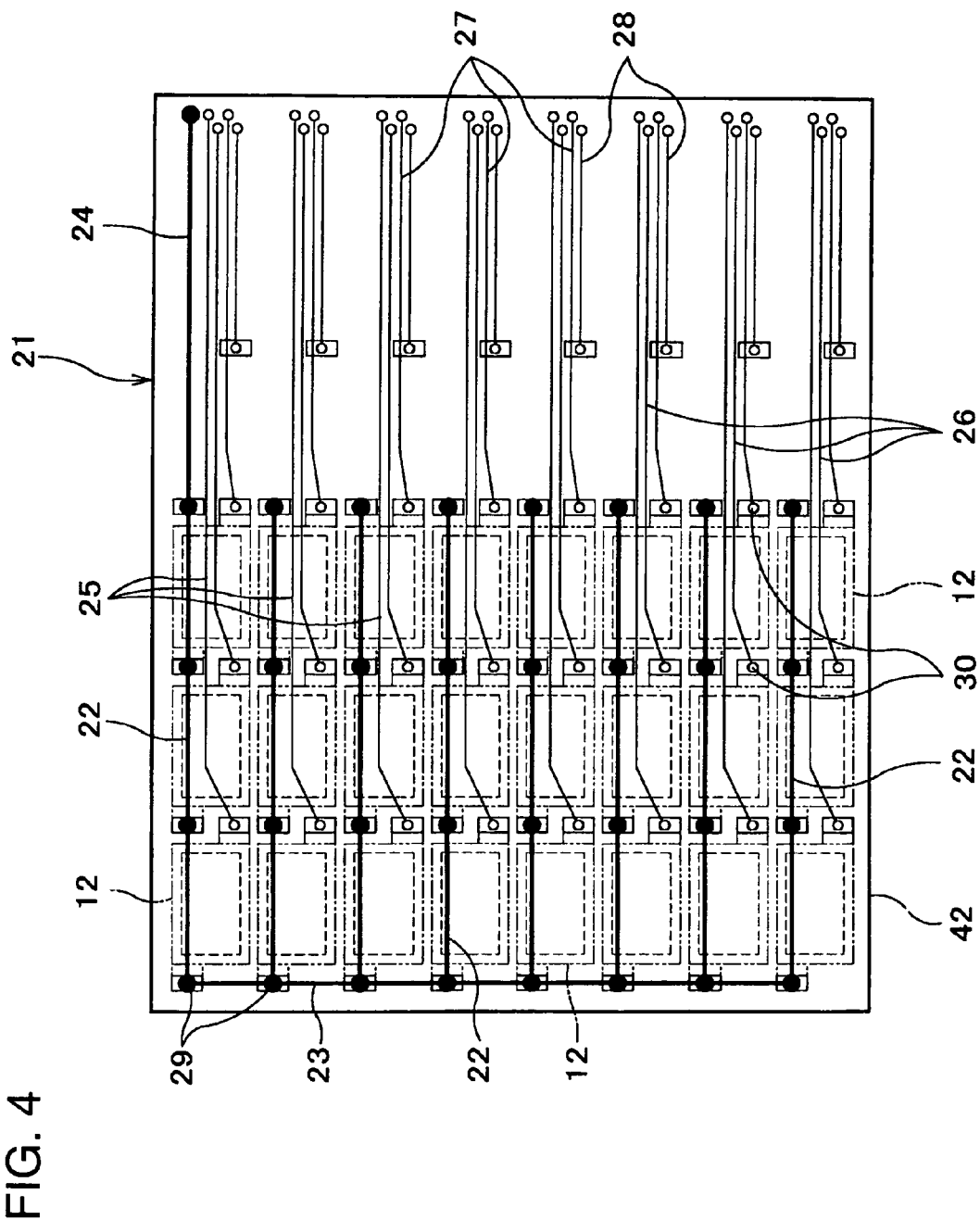
FIG. 4 is a plan view of a detector module using the semiconductor radiation detector according to the first embodiment of the present invention.

In FIG. 4, reference numeral 21 denotes a wiring board used for this embodiment and first cathode wirings 22 arranged in parallel to one another, a second cathode wiring 23 which extends perpendicular to the respective cathode wirings 22 and connects the cathode wirings 22 and a third cathode wiring 24 which extends rightward from the cathode wiring 22 at the top end in FIG. 4 are buried in this wiring board 21. These cathode wirings 22, 23 and 24 are electrically connected and the same potential is supplied from the outside of the wiring board 21 to the cathode electrodes 3 of all the detectors. The plurality of semiconductor radiation detectors 12 and the wiring board 21 in which these semiconductor radiation detectors 12 are arranged constitute a detector module 42. The detector module 42 also includes a plurality of cathode wiring and a plurality of anode wirings.

Furthermore, first anode wirings 25 arranged parallel to one another, second anode wirings 26 arranged parallel to one another, third anode wirings 27 arranged parallel to one another and fourth anode wirings 28 arranged parallel to one another are buried in the wiring board 21.

Figure 5:
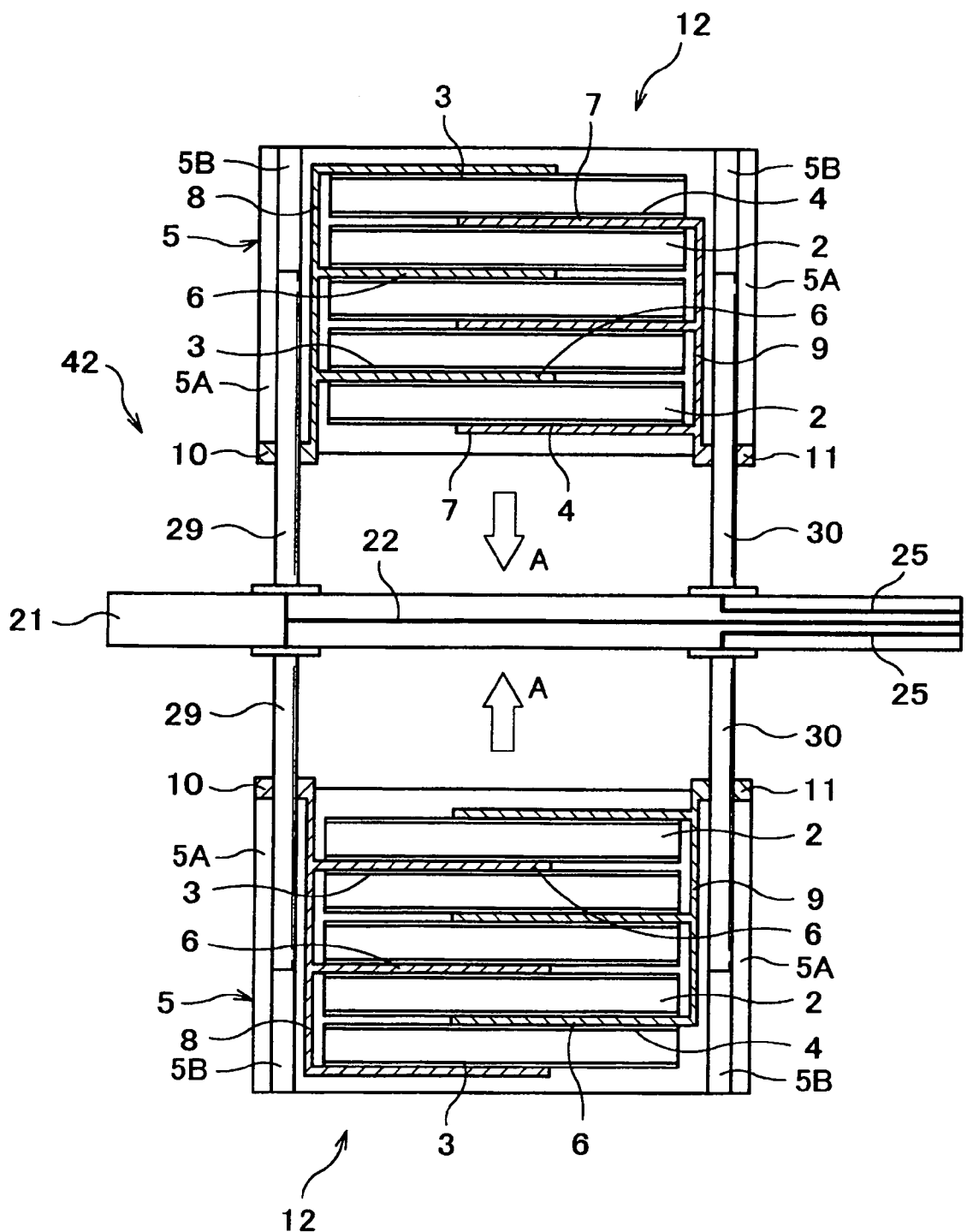
FIG. 5 is an assembly diagram of the detector module using the semiconductor detector according to the first embodiment of the present invention.

Then, as shown in FIG. 4 and FIG. 5, cathode pins 29 are formed in an upright position on the cathode wiring 22, spaced substantially uniformly on one side and the other side of the wiring board 21. Furthermore, anode pins 30 are also formed in an upright position at the ends of the first, second, third anode wirings 25, 26, 27 spaced substantially uniformly on one side and the other side of the wiring board 21.

Then, the semiconductor radiation detector 12 is inserted in a detachable manner in the direction indicated by an arrow A in FIG. 5 with a cathode pin 29 and an anode pin 30 fitted in the pin insertion holes 5B, 5B of the elastic insulator 5 with clamping margins. The semiconductor radiation detector 12 may also be directly fixed to the wiring board 21 using a conductive space, etc., instead of the cathode pin 29 and anode pin 30. In this case, instead of the pin insertion holes 5B, the insulator 5 is provided with plated wiring and the ends of this plated wiring are used as a cathode terminal 10 and an anode terminal 11. A conductive paste, etc., may be applied to these cathode terminal 10 and anode terminal 11, which may be then fixed to the wiring board 21.

Then, the operation of the semiconductor radiation detector 12 having such a structure will be explained.

A negative voltage is applied to the cathode electrodes 3 of the semiconductor device 2 from the outside of the wiring board 21 through the cathode wirings 22, 23, 24, a reverse bias voltage is formed between the cathode electrodes 3 and anode electrodes 4 of the semiconductor device 2 so that γ-rays can be measured. When γ-rays enter the semiconductor device 2, electric charge is induced between the cathode electrodes 3 and anode electrodes 4 set in the semiconductor device 2, and signals corresponding to the amount of charge induced are output from the anode wirings 25, 26, 27, 28 to the outside through a thin plate 7, internal wiring 9, anode terminal 11 and anode pin 30.

This embodiment allows γ-rays to be detected by separating their positions in the direction of incidence of γ-rays, too, and further allows γ-rays to be detected with their positions separated in the three-dimensional direction. Furthermore, covering with an insulator facilitates handling of the semiconductor radiation detector in manufacturing, etc., and can physically protect the radiation detection devices.

Furthermore, according to the method of using the cathode pin 29 and anode pin 30, the semiconductor radiation detector 12 is mounted on the wiring board 21 in a detachable manner, and it is possible to thereby replace any semiconductor radiation detector 12 and improve operability, etc., in the case of replacement.

Furthermore, the entire semiconductor device 2 is covered with the insulator 5, and therefore it is possible to produce the moisture-proof effect and light-shielding effect on the semiconductor radiation detector 12.

Second Embodiment

Figure 6:
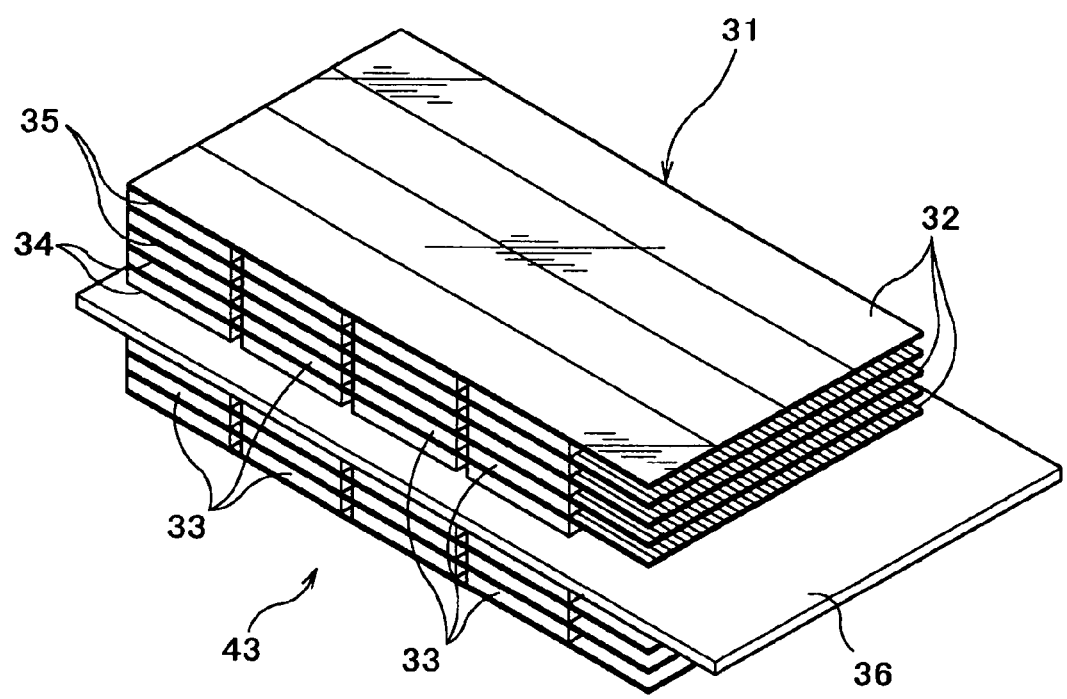
FIG. 6 is a perspective view of a detector module using a semiconductor detector according to a second embodiment of the present invention.

Then, a second embodiment of the present invention will be explained with reference to the attached drawings of FIG. 6 and FIG. 7. In FIG. 6, a plurality of semiconductor radiation detectors 31 are constructed by including thin wiring boards 32 with flexibility called "FPC (Flexible printed circuit)", semiconductor devices 33 mounted on both sides of the thin wiring boards 32, cathode electrodes 34 formed in a thin-film shape on one side of the semiconductor devices 33 through vapor deposition, etc., and anode electrodes 35 formed on the other side of the semiconductor devices 33.

The semiconductor devices 33 are arranged in four rows in the direction in which γ-rays propagate with a small gap interposed between neighboring devices and also arranged in four rows in the direction orthogonal to the direction in which γ-rays propagate with a small gap interposed between neighboring devices. Furthermore, the semiconductor radiation detectors 31 are mounted fixed to both sides of a thick wiring board (FR-4, etc.) 36. A plurality of semiconductor radiation detectors 31 mounted on both sides of the thick wiring board 36 constitute a detector module 43. Note that it is also possible to construct the semiconductor devices 33 using one crystal on the same plane and by dividing only the electrodes.

Figure 7:
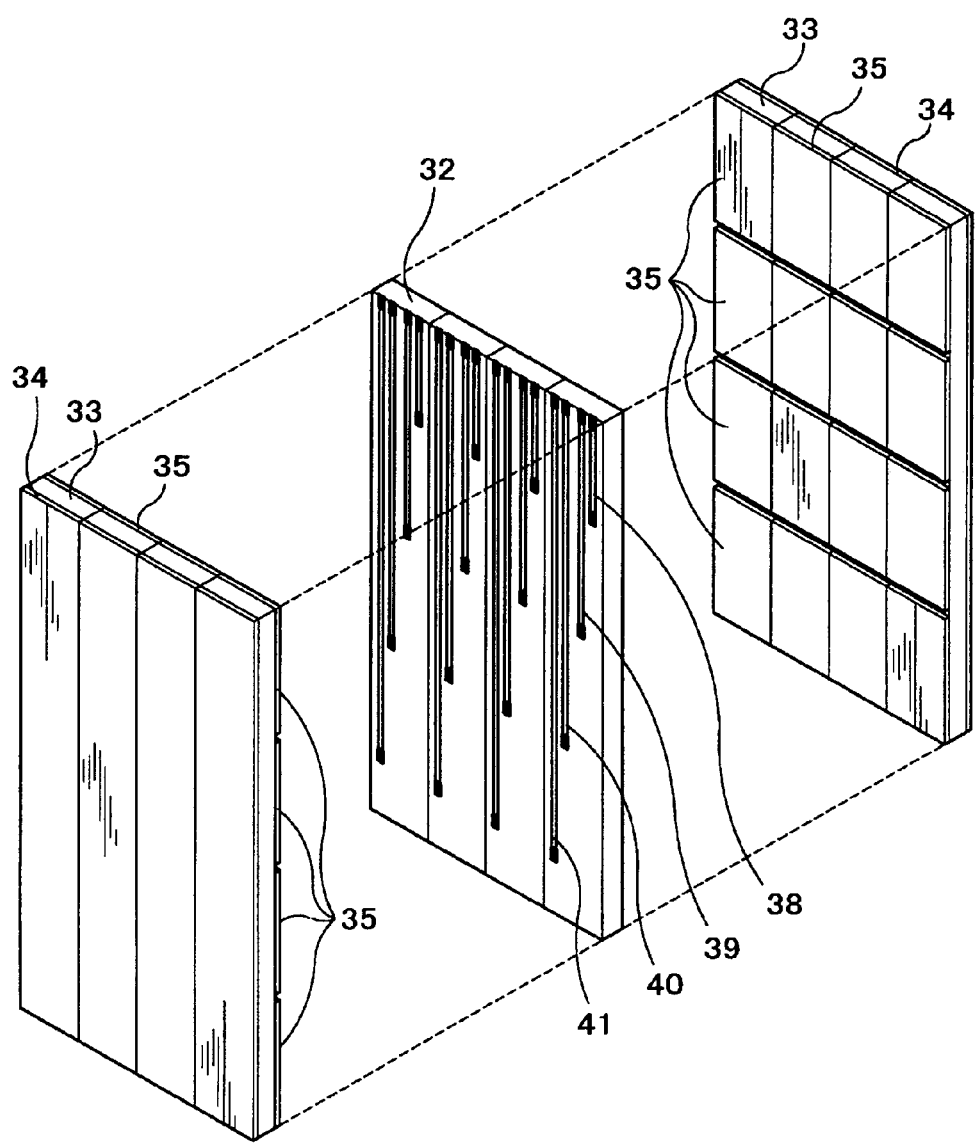
FIG. 7 is an exploded perspective view showing the semiconductor radiation detector in FIG. 6.

Furthermore, in the thin wiring boards 32 interposed between the facing anode electrodes 35, 35, four signal lines 38, 39, 40 and 41, which extend to the positions corresponding to the anode electrodes 35 of the respective semiconductor devices 33 to be connected to the respective anode electrodes 35 are buried as shown in FIG. 7.

On the other hand, in the thin wiring boards 32 interposed between the facing cathode electrodes 34, 34, supply lines (not shown) for applying a voltage common to all cathodes are buried in the cathode electrodes 34 and these signal lines are connected to the cathode electrodes 34 of the plurality of semiconductor devices 33 arranged along the direction of incidence of γ-rays.

The above described supply lines connected to the cathode electrodes 34 are connected to cathode wiring (not shown) of the thick wiring board 36 and the signal lines 38, 39, 40 and 41 are connected to the respective anode wirings (not shown) of the thick wiring board 36.

Note that the thick wiring boards 36 may be replaced by the thin wiring boards 32.

This embodiment having such a structure can also detect γ-rays by separating positions in the three-dimensional direction as with the first embodiment. Furthermore, it is also possible to reduce spacing between the plurality of semiconductor devices 31 and improve sensitivity.

Third Embodiment

Then, a third embodiment of the present invention will be explained with reference to the attached drawing of FIG. 8. The same components in this embodiment as those in the first embodiment are assigned the same reference numerals and explanations thereof will be omitted.

Figure 8:
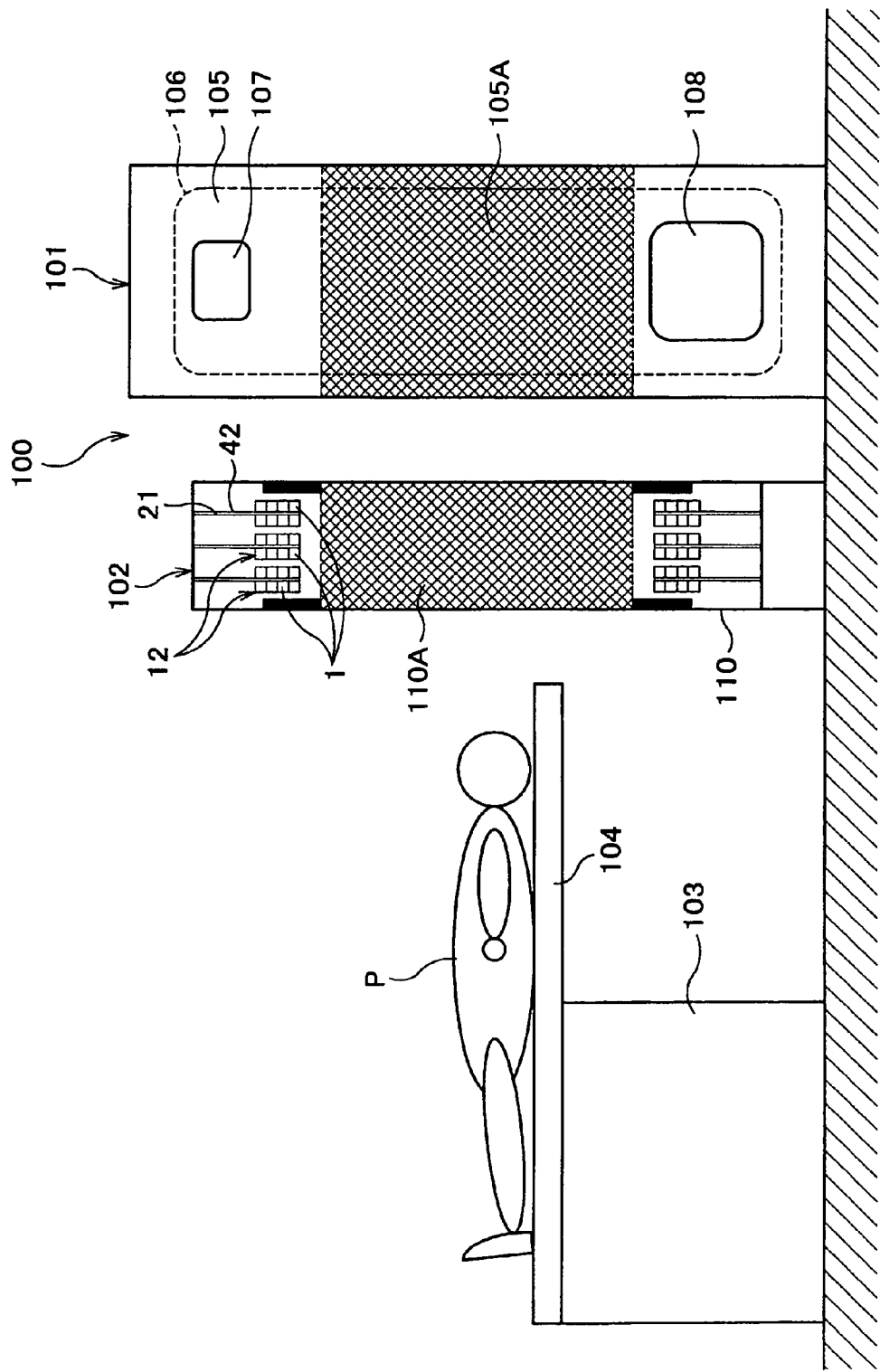
FIG. 8 is a longitudinal cross-sectional view of a PET-X-ray CT examination apparatus provided with a PET examination apparatus using the detector module in FIG. 4 according to a third embodiment of the present invention.

As shown in FIG. 8, a PET-X-ray CT examination apparatus 100, which is a radiation imaging apparatus, comprises an X-ray CT examination apparatus 101 and a PET examination apparatus 102 side by side. Furthermore, the PET-X-ray CT examination apparatus 100 includes a bed holding section 103 and a movable bed 104 provided on the bed holding section 103. Then, the X-ray CT examination apparatus 101 is provided with an X-ray CT gantry 105 having an opening 105A, a rotary section 106 rotatably mounted in the X-ray CT gantry 105, an X-ray generator 107 provided in the rotary section 106 and a radiation detector 108, which is a scintillator detector provided in the rotary section 106. Then, this X-ray CT examination apparatus 101 measures X-rays which are emitted from the X-rays generator 107 and have passed through an examinee P using a signal processing section (not shown) and obtains a mode image of the interior of the examinee P.

Furthermore, the PET examination apparatus 102 includes a PET gantry 110 having an opening 110A and the PET gantry 110 has a plurality of detector modules 42 arranged in the circumferential direction and axial direction. For this reason, a plurality of radiation detectors 12 are also arranged in the circumferential direction and axial direction of the PET gantry 110. The PET examination apparatus 102 is a radiation imaging apparatus which marks radionuclides which emit positrons through nucleorrhexis in chemicals, administers the chemicals into the examinee P, captures pairs of γ-rays having 511 keV energy which are emitted when pairs of positron and electron are annihilated in the body of the examinee P and creates images of them as functional images.

This embodiment having such a structure can mount the semiconductor radiation detectors 12 densely on both sides of the wiring board 21 as described in the conventional art, thereby increase the density of the semiconductor radiation detectors 12 per a unit length of the wiring board 21 in the detector module 42, improve the detection sensitivity and improve the performance and reliability of the PET-X-ray CT examination apparatus 100.

The PET examination apparatus 102 may also mount the detector module 43 shown in FIG. 6 in the PET gantry 110 instead of the detector module 42 as with the detector module 42.

As shown in FIG. 5, the first embodiment has described the case where the terminals of both the cathode terminal 10 and anode terminal 11 are exposed from one side of the insulator 5 which is a rectangular parallelepiped and the semiconductor radiation detectors 12 are fixed to both sides of the wiring board 21 using the cathode pin 29 and anode pin 30 as an example.

Figure 9:
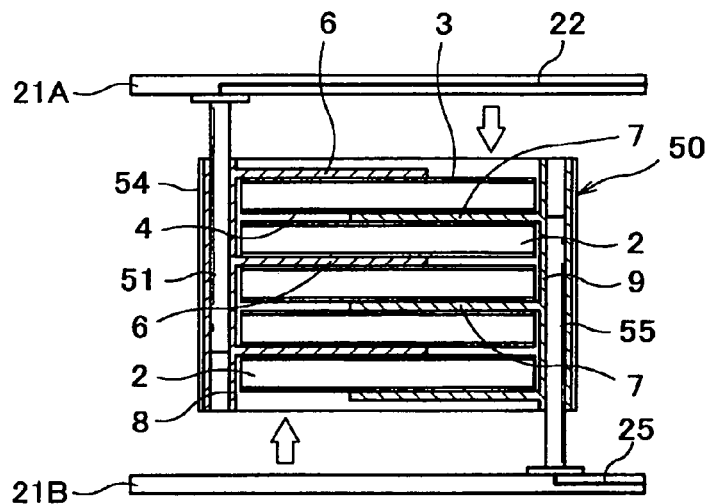
FIG. 9 is a cross-sectional view showing a semiconductor radiation detector according to a first modification example of the present invention.

However, the present invention is not limited to this but can be adapted so that as shown in a first modification example shown in FIG. 9, a cathode pin 51 is inserted from one side of an insulator 54 of a semiconductor radiation detector 50 and an anode pin 55 is inserted from the other side of the insulator 54 of the semiconductor radiation detector 50. In this case, the cathode pin 51 is connected to a cathode wiring 22 buried in a wiring board 21A and the anode pin 55 is connected to an anode wiring 25 buried in a wiring board 21B.

Figure 10:
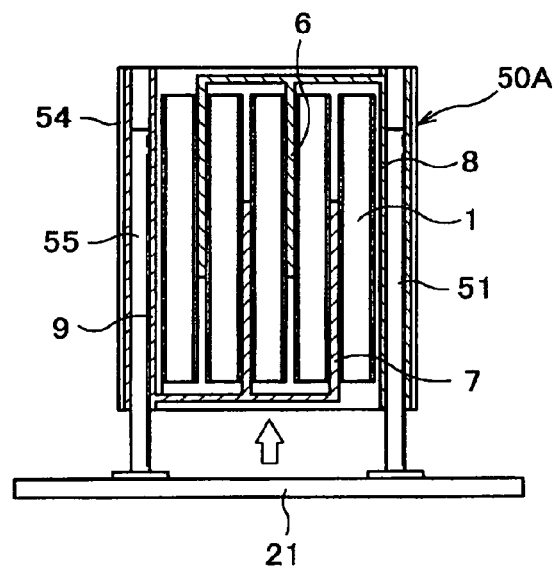
FIG. 10 is a cross-sectional view showing a semiconductor radiation detector according to a second modification example of the present invention.

Furthermore, for example, as a second modification example shown in FIG. 10, it is also possible to adopt a structure in which a semiconductor radiation detector 50A is placed in a direction perpendicular to a wiring board 21, and a cathode pin 51 and an anode pin 55 disposed on the wiring board 21 in an upright position are inserted into the semiconductor radiation detector 50A.

Figure 11:
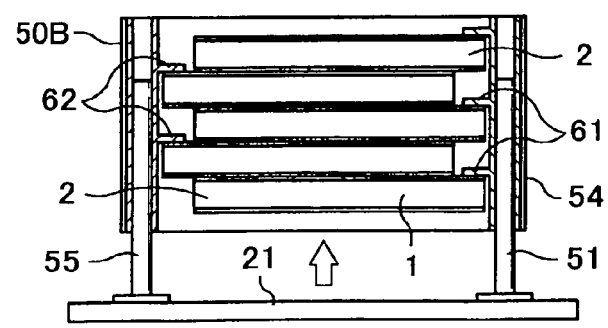
FIG. 11 is a cross-sectional view showing a semiconductor radiation detector according to a third modification example of the present invention.

Furthermore, in a semiconductor radiation detector 50B which is a third modification example shown in FIG. 11, a plurality of radiation detection devices 1 are arranged in a staggered configuration and internal wirings 62 are connected to anode electrodes of the radiation detection devices 1 protruding in one direction out of these radiation detection devices 1. Furthermore, internal wirings 61 are connected to cathode electrodes of the radiation detection devices 1 protruding in the other direction out of these radiation detection devices 1. The cathode pin 51 and anode pin 55 are connected to these internal wirings 61, 62.

Figure 12:
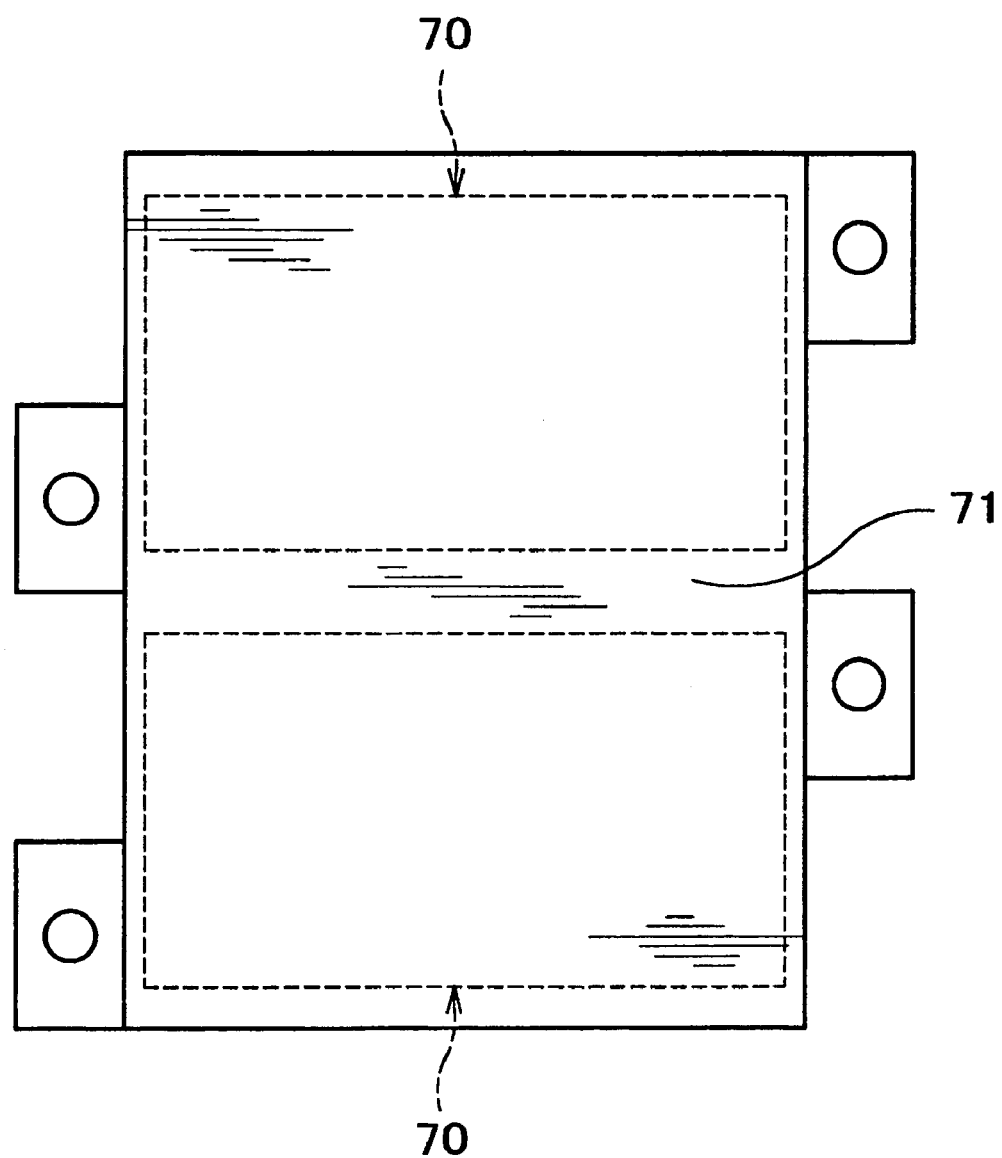
FIG. 12 is a plan view showing a semiconductor radiation detector according to a fourth modification example of the present invention.

The first embodiment has described the case where a plurality of semiconductor radiation detectors 12 are mounted on the wiring board 21 independently of one another through gaps as an example, but the present invention is not limited to this and can be adapted as a fourth modification example shown in FIG. 12 so that insulators 71 of neighboring semiconductor radiation detectors 70 are united.

Figure 13:
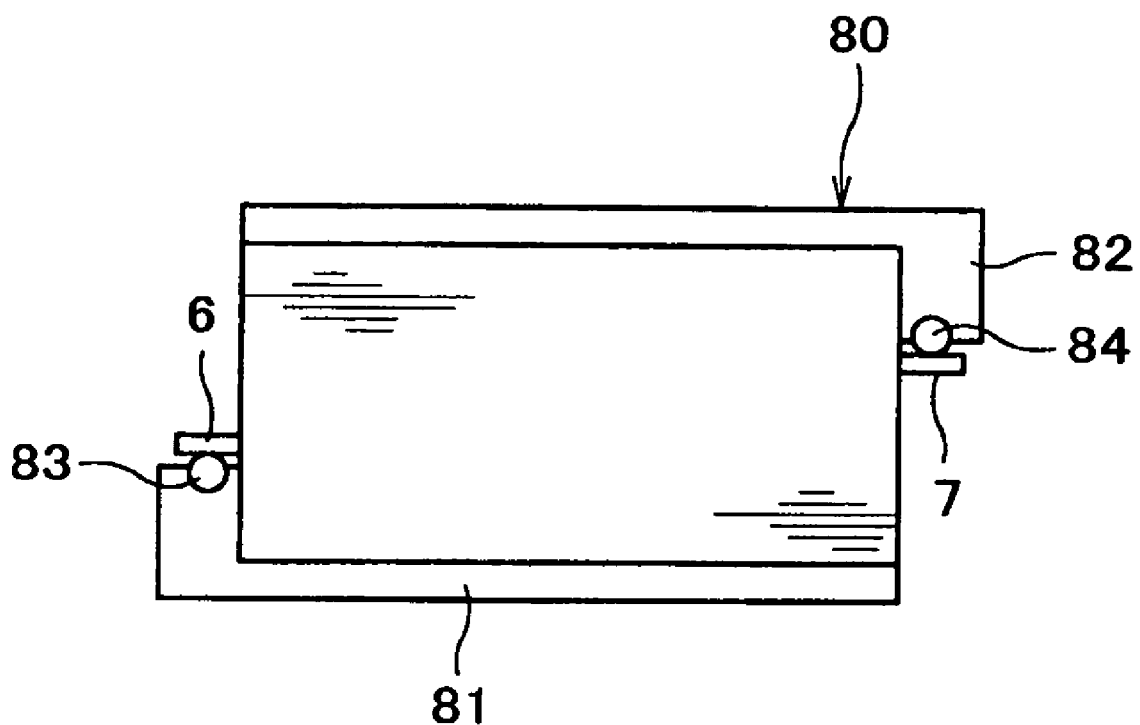
FIG. 13 is a plan view showing a semiconductor radiation detector according to a fifth modification example of the present invention.
Figure 14:
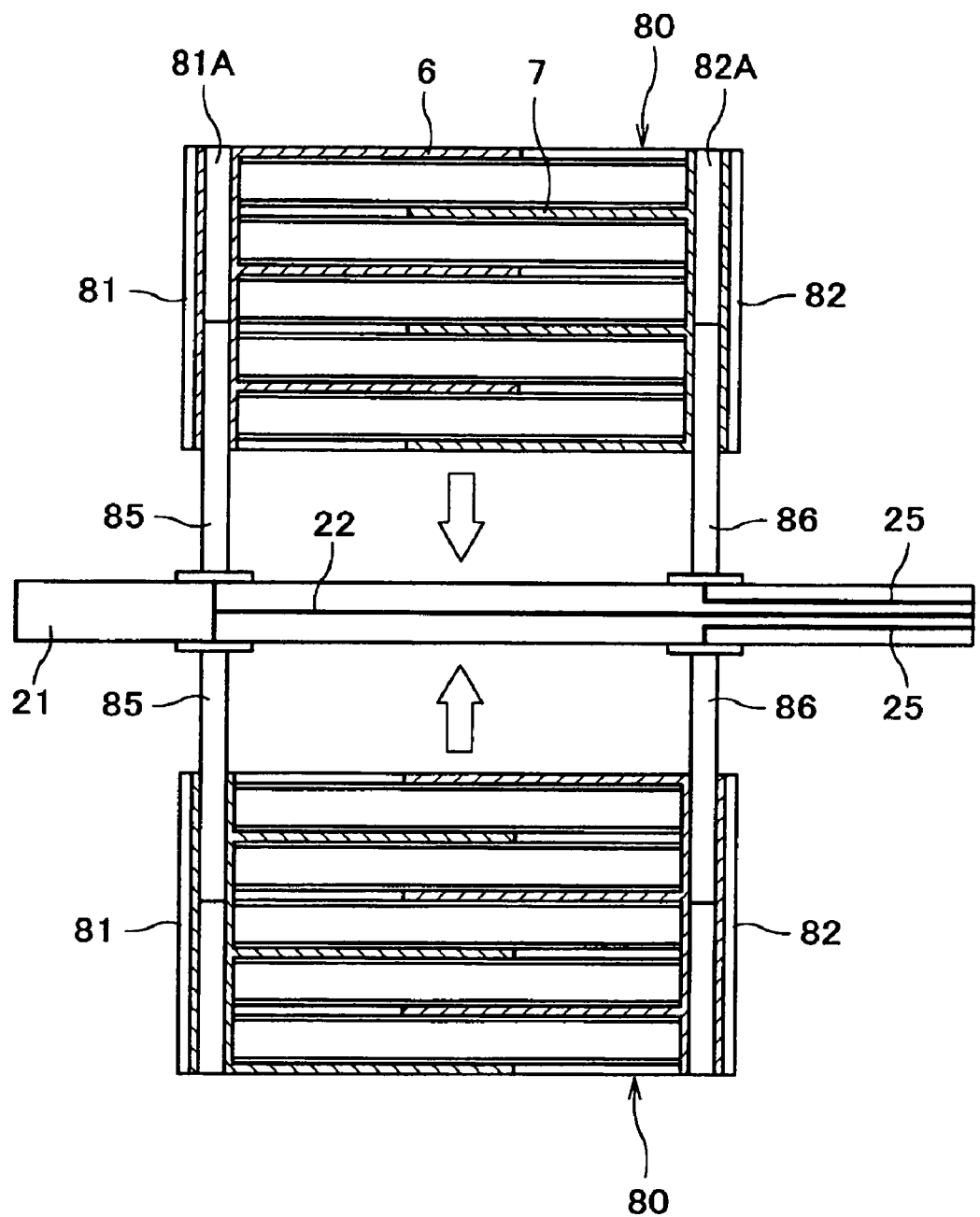
FIG. 14 is an assembly diagram showing the semiconductor radiation detector according to the fifth modification example of the present invention.

The first embodiment has also described the case where the entire semiconductor radiation detector 1 is coated with the insulator 5 as an example, but the present invention is not limited to this and can be adapted so that as in the case of a fifth modification example shown in FIG. 13 and FIG. 14, for example, a semiconductor radiation detector 80 is provided with insulators 81, 82 partially having pin insertion holes 81A, 82A and cathode socket (e.g., hollow metal pipe) 83 and anode socket 84 are provided inside the pin insertion holes 81A, 82A of this insulator 81 so that the cathode pin 85 is inserted into the cathode socket 83 and the anode pin 86 is inserted into the anode socket 84.

Figure 15:
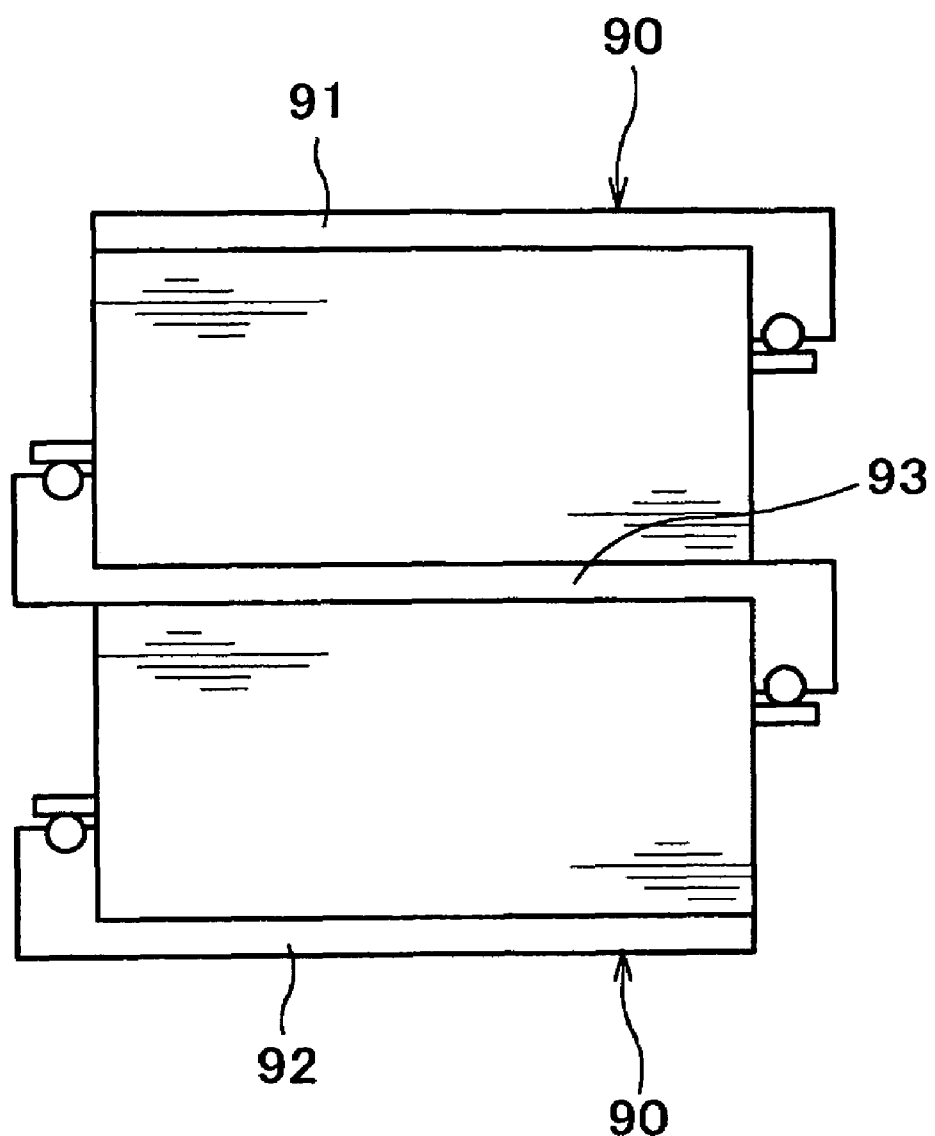
FIG. 15 is a plan view showing a semiconductor radiation detector according to a sixth modification example of the present invention.

In this case, it is also possible to adopt a structure as a sixth modification example shown in FIG. 15, for example, in which two neighboring semiconductor radiation detectors 90, 90 are partially provided with insulators 91, 92 and the two semiconductor radiation detectors 90, 90 are kept insulated from each other by means of a common insulating plate 93.

Figure 16:
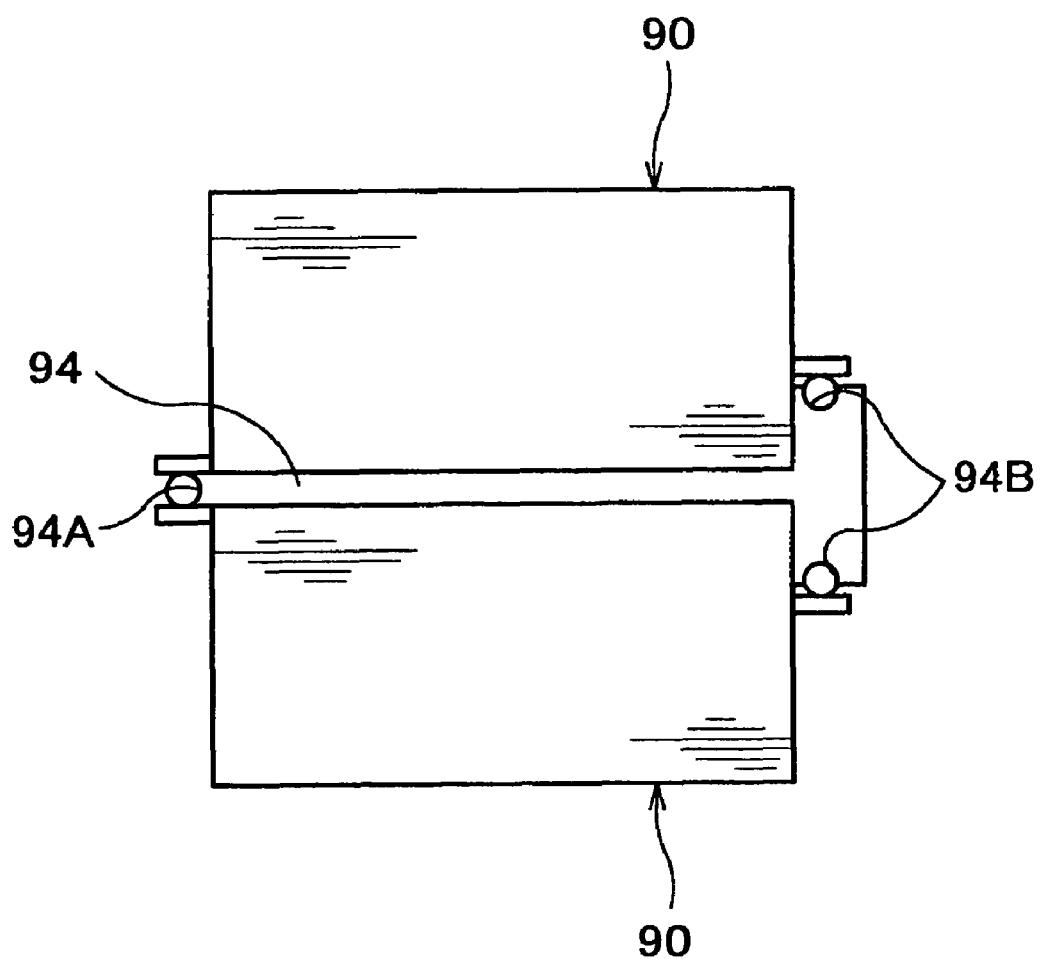
FIG. 16 is a plan view showing a semiconductor radiation detector according to a seventh modification example of the present invention.

Furthermore, it is also possible to adopt a structure as a seventh modification example shown in FIG. 16, for example, in which a pin insertion hole 94A on the cathode side is provided at one end of a common insulator 94 attached to two neighboring semiconductor radiation detectors 90 and pin insertion holes 94B, 94B on the anode side are provided at the other end of the insulator 94.

Figure 17:
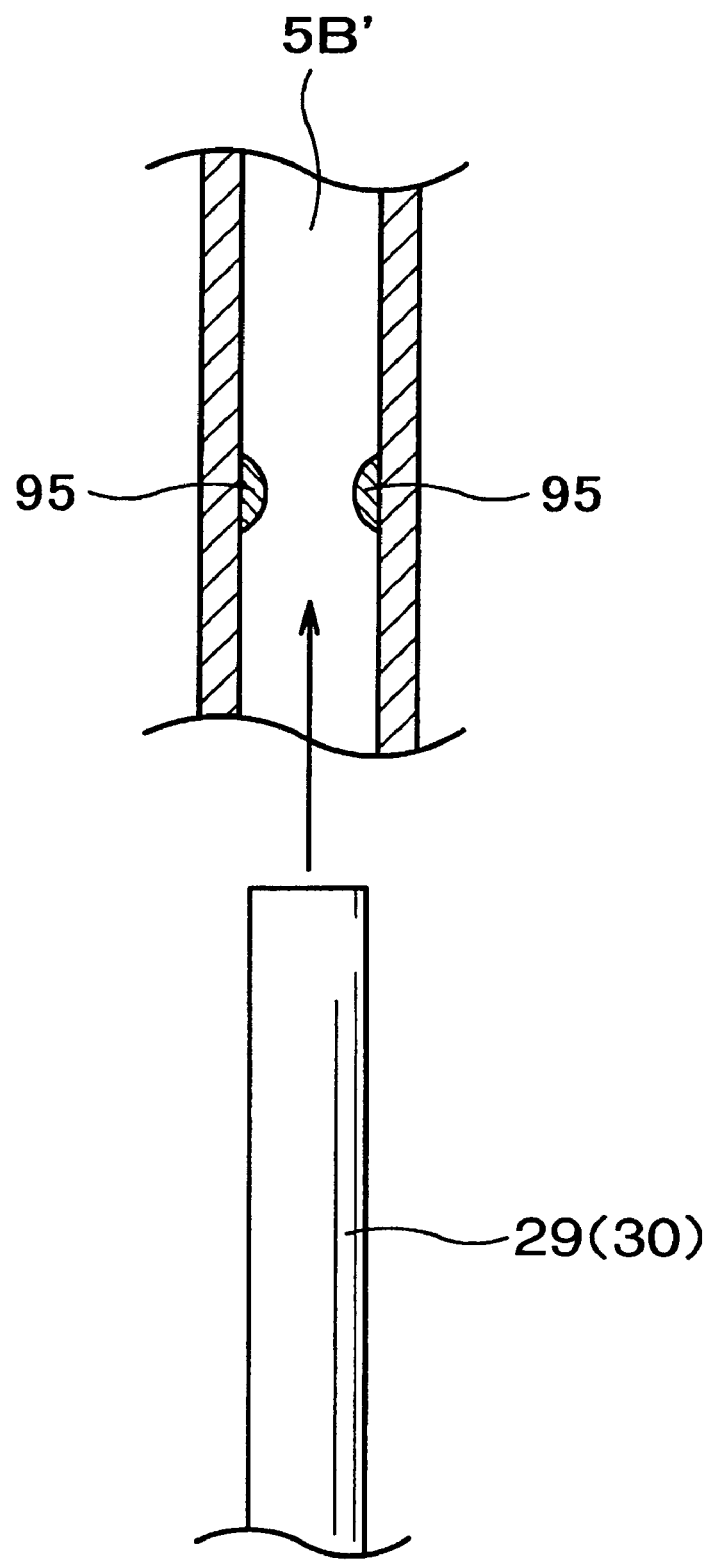
FIG. 17 is an exploded diagram showing a pin insertion hole and elastic bodies, etc., according to an eighth modification example of the present invention.

Moreover, the first embodiment has described the case where the cathode pin 29 and anode pin 30 having a slightly greater diameter than the diameter of the pin insertion holes 5B are fitted into these pin insertion holes 5B utilizing elasticity thereof as an example, but the present invention is not limited to this and, for example, as in the case of an eighth modification example shown in FIG. 17, hemispherical elastic bodies 95, 95 are attached to the inner surfaces of a pin insertion hole 5B' and a cathode pin 29 or anode pin 30 is inserted into a pin insertion hole 5B' in such a way as to be pushed by the elastic bodies 95, 95 from both sides.

In the above described modification examples, if detachability is not essential, it is possible to directly fix semiconductor radiation detectors to the wiring board using not the aforementioned cathode pin and anode pin but a conductive paste, etc. In this case, instead of pin insertion holes, plated wiring is applied to the insulator 5 and the ends of this plated wiring are used as a cathode terminal 10 and anode terminal 11. A conductive paste, etc., may be applied to this cathode terminal 10 and anode terminal 11 and fixed to the wiring board 21.

Furthermore, in the first embodiment, the output ends of the anode and cathode of the semiconductor radiation detector are arranged at diagonal positions of the semiconductor device, but their positions are not limited to this and their output ends may be arranged on the same side of the semiconductor detection device and a wiring pattern corresponding to the output end positions may be used for the wiring board in this case.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A detector module comprising:
    semiconductor radiation detectors; and
    a wiring board,
    said semiconductor radiation detectors comprising a plurality of semiconductor detection devices, each having a cathode electrode on one side of a semiconductor device and an anode electrode on the other, arranged in parallel in such a way that either said cathode electrodes or said anode electrodes of said neighboring semiconductor detection devices are opposed to each other and an insulator which coats at least some of said plurality of semiconductor detection devices from the outside is provided,
    wherein said cathode electrode is connected to a first wiring provided on said wiring board through a pin and said anode electrode is connected to a second wiring provided on said wiring board through another pin; and
    wherein said semiconductor radiation detector provided on one side of said wiring board and said other semiconductor radiation detector provided on the other side of said wiring board are opposed to each other with respect to said wiring board.

2. A detector module comprising:
    semiconductor radiation detectors; and
    a wiring board,
    said semiconductor radiation detectors comprising a plurality of semiconductor detection devices, each having a cathode electrode on one side of a semiconductor device and an anode electrode on the other side, arranged in parallel, an insulator which coats at least a portion of said semiconductor detection devices from the outside, a first internal wiring which is disposed inside said insulator or on the surface thereof and connected to said respective cathodes and a second internal wiring which is disposed inside said insulator or on the surface thereof and connected to said respective anodes,
    wherein said first and second internal wirings are connected to corresponding wirings of said wiring board by a cathode pin and an anode pin, and
    wherein said semiconductor radiation detector is disposed on said wiring board; and
    wherein said semiconductor radiation detector disposed on one side of said wiring board and said other semiconductor radiation detector disposed on the other side of said wiring board are opposed to each other with respect to said wiring board.

3. A radiation imaging apparatus comprising the detector module according to any one of claim 1 and claim 2 and a bed for supporting an examinee.

4. The radiation imaging apparatus according to claim 3, comprising:
    a positron emission tomography apparatus in which a plurality of said detector modules are disposed so as to surround said bed; and
    an X-ray CT apparatus, wherein said positron emission tomography apparatus and said X-ray CT apparatus are disposed in a longitudinal direction of said bed, and said bed is shared by said positron emission tomography apparatus and said X-ray CT apparatus.

5. A positron emission tomography apparatus comprising:

the detector module according to any one of claim 1 and claim 2; and a bed for supporting an examinee, wherein a plurality of said detector modules are disposed so as to surround said bed.

6. The detector module according to claim 2, wherein said cathode pin and said anode pin are arranged on a diagonal line of said semiconductor radiation detector.

* * * * *